(12) United States Patent
Chen et al.

(10) Patent No.: US 11,459,294 B2
(45) Date of Patent: Oct. 4, 2022

(54) METHOD AND SYSTEM FOR REMOVING IMPURITIES OUT OF TAURINE MOTHER LIQUOR AND TAURINE MOTHER LIQUOR RECOVERY

(71) Applicant: QIANJIANG YONGAN PHARMACEUTICAL CO LTD, Qianjiang (CN)

(72) Inventors: Yong Chen, Qianjiang (CN); Xiquan Fang, Qianjiang (CN); Feng Liu, Qianjiang (CN); Shaobo Li, Qianjiang (CN)

(73) Assignee: QIANJIANG YONGAN PHARMACEUTICAL CO LTD, Hubei Province (CN)

( * ) Notice: Subject to any disclaimer, the term of this patent is extended or adjusted under 35 U.S.C. 154(b) by 0 days.

(21) Appl. No.: 17/008,353

(22) Filed: Aug. 31, 2020

(65) Prior Publication Data

US 2021/0061758 A1    Mar. 4, 2021

(30) Foreign Application Priority Data

Sep. 2, 2019   (CN) .......................... 201910826732.9

(51) Int. Cl.
*C07C 303/44*   (2006.01)
*C07C 303/02*   (2006.01)
(Continued)

(52) U.S. Cl.
CPC .......... *C07C 303/44* (2013.01); *B01D 15/363* (2013.01); *C07C 303/02* (2013.01); *C07C 309/14* (2013.01)

(58) Field of Classification Search
None
See application file for complete search history.

(56) References Cited

U.S. PATENT DOCUMENTS 2,693,488 A    11/1954 Sexton
10,604,478 B1 *  3/2020 Sun ........................ C07C 303/44

FOREIGN PATENT DOCUMENTS

| CN | H0421666 | * | 1/1992 |
| CN | 105732440 | * | 7/2016 |
| EP | 3415497 A1 | | 12/2018 |

OTHER PUBLICATIONS

Wikipedia entry for "Alkali", downloaded from https://en.wikipedia.org/wiki/Alkali on Sep. 15, 2021 (Year: 2021).*

(Continued)

*Primary Examiner* — Amy C Bonaparte
(74) *Attorney, Agent, or Firm* — Porter Wright Morris & Arthur LLP

(57) ABSTRACT

A method for removing impurities from a taurine mother liquor and recovering the taurine mother liquor. The method is used in an ethylene oxide production process for taurine. The last mother liquor of taurine is ion-exchanged through an anion exchange resin; then the anion exchange resin is eluted and regenerated with alkaline solution, and the eluate is collected. The eluate is subjected to ammonia mixing treatment, and the treated mother liquor is generated after the impurity is removed from the eluate by solid-liquid separation. The treated mother liquor can then be returned to the ammonolysis step of taurine production.

12 Claims, 7 Drawing Sheets

(51) Int. Cl.
*B01D 15/36* (2006.01)
*C07C 309/14* (2006.01)

(56) References Cited

OTHER PUBLICATIONS

Wikipedia entry for "Ion-exchange resin", downloaded from https://en.wikipedia.org/wiki/Ion-exchange_resin on Sep. 16, 2021 (Year: 2021).*

SciFinder entry for Isethionic acid, downloaded on Sep. 15, 2021 (Year: 2021).*

* cited by examiner

METHOD AND SYSTEM FOR REMOVING IMPURITIES OUT OF TAURINE MOTHER LIQUOR AND TAURINE MOTHER LIQUOR RECOVERY

BACKGROUND

The present disclosure relates to a production method for chemically synthesizing taurine, in particular to a mother liquor produced during the production of taurine by the ethylene oxide method, a method for removing impurities from the mother liquor and recycling the mother liquor, and a production system thereof.

BACKGROUND OF THE INVENTION

Taurine (2-aminoethanesulfonic acid) is the most abundant sulfur-containing free amino acid in the body's cells. The chemical synthesis of taurine mainly includes an ethylene oxide method and an ethanolamine method. Among them, the ethylene oxide process includes three steps:

(1) Using ethylene oxide as the starting material, the addition reaction of ethylene oxide and sodium bisulfite to generate sodium isethionate:
Main Reaction:

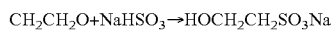
$CH_2CH_2O+NaHSO_3 \rightarrow HOCH_2CH_2SO_3Na$

Addition Side Reaction:

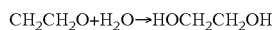
$CH_2CH_2O+H_2O \rightarrow HOCH_2CH_2OH$ (2) Ammonolysis of sodium isethionate to generate sodium taurate:

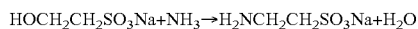
$HOCH_2CH_2SO_3Na+NH_3 \rightarrow H_2NCH_2CH_2SO_3Na+H_2O$

Ammonia hydrolysis side reactions:

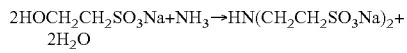
$2HOCH_2CH_2SO_3Na+NH_3 \rightarrow HN(CH_2CH_2SO_3Na)_2+ 2H_2O$

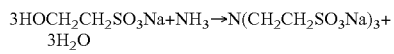
$3HOCH_2CH_2SO_3Na+NH_3 \rightarrow N(CH_2CH_2SO_3Na)_3+ 3H_2O$ (3) Taurine is generated through acidification, such as by using hydrochloric acid or, more typically, sulfuric acid to neutralize the sodium taurate and generate taurine and inorganic salts. For example, when sulfuric acid is used, a taurine solution is produced:

$2H_2NCH_2CH_2SO_3Na+ H_2SO_4 \rightarrow 2H_2NCH_2CH_2SO_3H+Na_2SO_4$ By-products are inevitably produced in the above addition and synthesis reactions, including ethylene glycol, ethylene glycol polymers and the like. The ammonolysis reaction is a reversible reaction. About more than 20% of sodium isethionate will enter step 3 of the production process. After the ammonia solution is neutralized by sulfuric acid (or another acid) in step 3, crude taurine is separated from the mother liquor. The mother liquor is concentrated and crystallized for 1-3 times, with crude taurine separated and extracted from the mother liquor after each crystallizing step, thereby generating the last mother liquor. Thus, the "last mother liquor" is the solution remaining after the mother liquor has been concentrated and solid taurine crystallized and removed at least once. In some instances the concentration/crystallization process is repeated at least one time more or at least two times more to generate the last mother liquor. The last mother liquor will mainly include taurine, along with sodium isethionate and the impurities sodium sulfate, sodium iminodisulfonate, ethylene glycol and polyethylene glycol, and trace metal ions, which are highly polluting emissions. The last mother liquor will also include sodium ditaurate ($HN(CH_2CH_2SO_3)Na)_2$) and sodium tritaurate ($N(CH_2CH_2SO_3)Na)_3$). When the existing production method adopts the mother liquor circulation, the cumulative increase of by-products will occur. When the by-products reach a threshold level, discharging part of the mother liquor is necessary, resulting in waste and pollution.

Chinese patents CN101508657, CN10158658, CN10158659 and CN101486669 describe a method for neutralizing sodium taurate with sulfuric acid to generate taurine and sodium sulfate. After cooling, the crude taurine can be easily generated by filtering the crystal suspension. However, the waste mother liquor still contains taurine, sulfate and other organic impurities.

On the use of mother liquor, "Research on Taurine Ammonolysis Process", published in Issue 5, Volume 44 of Shandong Chemical Industry, 2015, (Author: Liu Fuming, Xie Limin), specifies in detail the process of taurine reaction, and the other organic impurities in the reaction, such as ethylene glycol and polyethylene glycol, and analyzes the effect of mother liquor application on yield. The higher the content of mother liquor in the reaction system, the higher the product yields. In the actual production process, the amount of mother liquor cannot be infinitely increased. As the content of mother liquor increases, by-products in the reaction system increase greatly, and the output of the last mother liquor in the production process can only meet the maximum 9.0% (v/v) set of dosage. Considering comprehensive production costs and yield quality, it is most appropriate to choose the mother liquor content of 6.3%-8.3% (v/v). Therefore, the removal of impurities in the mother liquor is a prerequisite for increasing the application of the mother liquor, otherwise the increase in the amount of application will cause more by-products in production and the production will be more unstable.

Chinese patent CN107056659A describes a method for neutralizing sodium taurate by ion exchange to generate taurine, and then recycling the mother liquor to further increase the yield. This process route mainly avoids the generation of sulfate, recycles sodium atoms therein, and greatly saves raw materials such as sulfuric acid and sodium hydroxide, wherein the extracted mother liquor is returned to the ammonolysis reaction as a raw material. However, the process does not avoid the occurrence of side reactions such as addition and synthesis reactions, and the mother liquor still needs to be subjected to impurity removal treatment.

With regard to the impurity removal treatment of the mother liquor, Chinese patent CN105732440 discloses a method for producing taurine by fully recovering the mother liquor, which mainly removes impurities by neutralization in the second stage to obtain crude taurine, and the mother liquor is subjected to pressure filtration and catalysis to further remove sodium sulfate. After that, the sodium is reused in the synthesis section. Among them, the removal effect of ethylene glycol and other organic polymers therein by the second-stage neutralization and removing impurities is limited.

In summary, although the current taurine preparation process is relatively mature, there are still many deficiencies in the separation and purification of taurine and the recycling of mother liquor, and an effective solution is urgently needed.

SUMMARY

The present disclosure provides an impurity removal and recovery process and production system, which can effectively remove impurities in the last mother liquor of taurine and recycle the last mother liquor. In this manner, the last mother liquor can be recycled to the taurine synthesis section, thereby reducing environmental pollution caused by the discharge of mother liquor and improving product yield.

Through a lot of researches and experiments, the inventors have unexpectedly discovered a method for removing impurities and recovering taurine mother liquor, which can recover all of the mother liquor in the existing ethylene oxide process for preparing taurine after removing impurities.

The present disclosure provides a method for removing impurities from and recovering taurine mother liquor, which can be applied to the taurine production process by the ethylene oxide method, to process the last mother liquor of taurine. As noted previously, the last mother liquor of taurine refers to the taurine mother liquor that has been concentrated and separated at least once. The method includes the following steps:

(a) the last mother liquor of taurine is ion-exchanged using an anion exchange resin, and the effective components (taurine anion, and the anions of sodium isethionate, sodium ditaurate, and sodium tritaurate) are adsorbed on the anion exchange resin; then the anion exchange resin is eluted and regenerated with an alkali solution, and the outlet material liquor (the eluate) is collected;
(b) ammonia mixing treatment is performed on the outlet material liquor collected in step (a), and solid-liquid separation is then performed to generate the mother liquor after removing impurities (the treated mother liquor); and
(c) the treated mother liquor generated in step (b) is returned to the ammonolysis step.

During the ammonia mixing treatment, liquid ammonia or ammonia gas is added to the outlet material liquor, and the mass-volume ratio of ammonia is 15 g/100 ml or more.

In one embodiment, the anion exchange resin is an alkaline anion exchange resin.

In some instances, before step (a), the last mother liquor of taurine is decolorized and impurities removed using activated carbon by the steps comprising:
activated carbon is added to the last mother liquor of taurine under reduced temperature conditions, and impurities are then removed from the last mother liquor by solid-liquid separation (e.g., filtration); the pH of the solution following solid-liquid separation is then adjusted to acidic or neutral.

The pH value of the last mother liquor solution of taurine after activated carbon treatment is adjusted with sulfuric acid or other acid to 2.5-7.0. Alternatively, instead of using an acid to adjust the pH value, before or after the solid-liquid separation the pH value of the last mother liquor of taurine solution is adjusted using a cation exchange resin, such that the pH value is adjusted to 3.0-6.0, or 3.0-3.5.

The reduced temperature condition during treatment with activated carbon means that the temperature of the production system is lower than the temperature of the previous step. For example, the system processing temperature during the treatment with activated carbon is controlled between 15-25° C., or 18-22° C.

Applying the above method for removing impurities and recovering the mother liquor in an ethylene oxide taurine production process, includes the following steps:
S1. ethylene oxide reacts with sodium bisulfate solution to generate sodium isethionate;
S2. mix the sodium isethionate generated in S1, the recycled treated mother liquor, and ammonia (e.g., ammonia water) to generate the reaction solution; the ammonia is absorbed to a certain concentration, an ammonolysis reaction is carried out under the action of a catalyst, and a sodium taurate solution is generated after evaporation and concentration;
S3. the sodium taurate solution generated in S2, following evaporation and concentration, is treated with an acidic cation exchange resin to generate a taurine solution; as an alternative to using an acidic cation exchange resin, sulfuric acid is added to the evaporated and concentrated sodium taurate solution from step S2 to reach a pH value of 7.0-8.5, thereby generating a taurine crystallization solution;
S4. the taurine solution generated using an acidic cation exchange resin in S3 is concentrated and crystallized to generate crude taurine and mother liquor, and the (first) crude taurine is removed from the (first) mother liquor; when S3 uses sulfuric acid to generate taurine, the crude taurine is separated from the first mother liquor after cooling and crystallizing; in either instance, the mother liquor is then concentrated and crystallized for multiple times, with taurine separated and extracted from the mother liquor, such as through filtering equipment (e.g., a plate and frame device), and the remaining liquid is concentrated to generate the last mother liquor of taurine;
S5. the last mother liquor of taurine collected in S4 is cooled to 15-25° C., then a certain amount of activated carbon is added; sulfuric acid is added to adjust the pH value to 2.5-7.0, and the mother liquor is separated through filtering equipment such as a plate and frame device and a microporous filter; as an option, instead of adding sulfuric acid to adjust the pH value, acid reduction treatment is performed using an acidic cation exchange resin before or after solid-liquid separation;
S6. the mother liquor collected in S5 is passed over an alkali anion exchange resin, and the anion exchange resin exchanges with taurine and sodium isethionate in the last mother liquor, as well as sodium ditaurate, and sodium tritaurate, such that the anions of these components are absorbed onto the resin, leaving an impurity-containing liquid at the collection outlet (which requires subsequent processing); after collection to a certain extent, the resin is regenerated with an alkaline solution and the outlet material liquor (the eluate) is collected as the treated taurine mother liquor (i.e., the last mother liquor of taurine after impurities have been removed);
S7. combine the treated taurine mother liquor collected in S6 with liquid ammonia or ammonia gas under cooling conditions until the mass-volume ratio of ammonia is greater than 15 g/100 ml; a large amount of sulfate and other impurities will be precipitated, and these can be filtered out using a leaf filter or a closed plate and frame device to generate the clear, treated mother liquor; the treated mother liquor generated can be returned to step S2 and used in the ammonolysis step.

It should be noted that the sodium isethionate produced in S1 can be concentrated and crystallized and dried to generate the corresponding solid, or, after the direct reaction in S1 is completed, the mixed liquid generated by the reaction can be directly mixed with the ammonia in S2. In one embodiment, the reaction solution in S2 has a concentration of ammonia of 20-28 wt % (weight percent) after ammonia absorption.

In one embodiment, the concentration of the sodium bisulfite solution in S1 is 9-36 wt %, and the ratio of the amount of sodium bisulfite to the amount of ethylene oxide is 1:0.95-1.

In one embodiment, the catalyst used in S2 is any one of, or the mixture of any two or more of, sodium hydroxide, potassium hydroxide, lithium hydroxide, sodium carbonate, potassium carbonate, and lithium carbonate, and the temperature of the ammonolysis reaction is 150-290° C., and the pressure is 10-25 MPa.

In one embodiment, when the acid cation exchange resin column treatment is used to treat sodium taurate in S3, the concentration of the sodium taurate solution is adjusted to 15%-35%, or 18%-20% prior to treatment by the resin. In S3, when sulfuric acid is used to treat sodium taurate, the concentration of the sodium taurate solution is adjusted to 25%-40%, or 32%-38%.

To produce finished taurine, the crude taurine recovered in S4 is dissolved in water, activated carbon added, etc., then decolorized, filtered, cooled, crystallized, and dried after centrifugation to generate the finished taurine product. The refined mother liquor after centrifugation can be reused to prepare the sodium taurate solution or used in the decolorization of crude taurine (as shown in FIGS. 7 and 8).

In S4, after the initial removal of the first crude taurine from the taurine solution of S3, the mother liquor is concentrated and crystallized multiple times. to For example, the mother liquor can be concentrated and crystallized, with crude taurine removed each time, twice or three times. For example, the last mother liquor of the generated taurine may be the second mother liquor (i.e., mother liquor concentrated and crystallized once after the first removal of crude taurine) or the third mother liquor. When S3 uses an acidic cation exchange resin column for the treatment of sodium taurate, the last mother liquor of taurine can be the second mother liquor; when sulfuric acid is used in the treatment of sodium taurate in S3, the last mother liquor of taurine can be the third mother liquor.

Based on the impurity removal and recovery method of the present disclosure, a system for processing the last mother liquor of taurine in the ethylene oxide process of taurine production process to remove impurities and recover the mother liquor is provided. This system includes an anion resin adsorption device and an ammonia mixing and desalination device, connected successively, to adsorb the effective components. The feed port of the anion resin adsorption device can be connected to the outlet for the last mother liquor of taurine. The anion resin adsorption device can be provided with an anion exchange resin column. The ammonia mixing and desalination device can include an ammonia mixing reaction tank provided with a circulation path and a sealed filtering device.

In one embodiment, an activated carbon decolorization and impurity removal device is provided between the anion resin adsorption device and the discharge port for the last mother liquor of taurine. The activated carbon decolorization and removing impurity device includes a decolorization tank and a filtration device.

In one embodiment, the upstream end or the downstream end of the activated carbon decolorization and impurity removal device is connected to a cationic resin adsorption device, and the cationic resin adsorption device is used to reduce the pH value of the last mother liquor of taurine.

In one embodiment, when the downstream end of the activated carbon decolorization and impurity removal device is connected to a cationic resin adsorption device, the cationic resin adsorption device includes a raw material tank and a cation exchange resin column, and the raw material tank and the output of the activated carbon decolorization and impurity removal device are connected. The cation exchange resin column and the anion exchange resin column are connected.

In one embodiment, the anion exchange resin column controls the addition of alkaline liquor through a regeneration feed valve and absorbs the anions on the anion exchange resin, and the absorbed anions are eluted and collected in a mother liquor receiving tank through a regeneration manner; the outlet of the mother liquor receiving tank is connected to the feed port of the ammonia mixing and desalination device.

In one embodiment, the ammonia mixing reaction tank is provided with an ammonia inlet, a feed inlet and a discharge outlet, and the outlet of the ammonia mixing reaction tank is connected to the feed inlet of the sealed filtering device through a pump, and a transfer discharge valve is provided with the pump to discharge the filtered clear material.

In one embodiment, the anion resin adsorption device includes a raw material tank, a raw material pump, an anion exchange resin column, and a receiving tank which are sequentially connected, wherein the raw material tank and the receiving tank are both atmospheric pressure devices.

In one embodiment, the anion exchange resin column is an alkali anion exchange resin column.

In one embodiment, the sealed filtering device is a leaf filter or a sealed plate and frame filter.

In one embodiment, the activated carbon decolorization and impurity removal device includes a decolorization tank, a primary filtration device, a transit tank, a secondary filtration device, and a receiving storage tank that are connected in sequence. In one particular embodiment, the decolorization tank is provided with a temperature reduction mechanism, and the secondary filtration device is a precision filter.

In one embodiment, the temperature reduction mechanism is a water circulation condensing layer, also referred to as a water jacket, provided on the outside of the decolorization tank, and the cooling water inlet and outlet valves control the inflow and outflow of the water used for cooling.

In one embodiment, the primary filtering device is a plate and frame filter or a microporous filter.

Compared with the current technology, embodiments of the methods and systems of the present disclosure provide one or more of the following advantages and beneficial effects:

1. The methods and systems of the present disclosure, after treating the last mother liquor of taurine with an anion exchange resin, can remove more impurities in the taurine mother liquor, and remove the salt further by ammonia mixing treatment to generate the pure taurine mother liquor, thus realizing the increase of recycling of mother liquor and increase of the product yield.

2. The activated carbon decolorization and impurity removal device used in embodiments of the present disclosure, under cooling conditions, uses activated carbon to adsorb a certain amount of impurities such as ethylene glycol, metal ions, and a small amount of organic matter, so that the impurities in the taurine mother liquor can be removed more thoroughly.

3. The impurity removing and recovery systems of the present disclosure adopt an optimized design and use the impurity removal device to remove various impurities contained in the last mother liquor in a targeted manner, which is efficient and thorough, simple in operation, and low in operation costs.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

Figure 1:
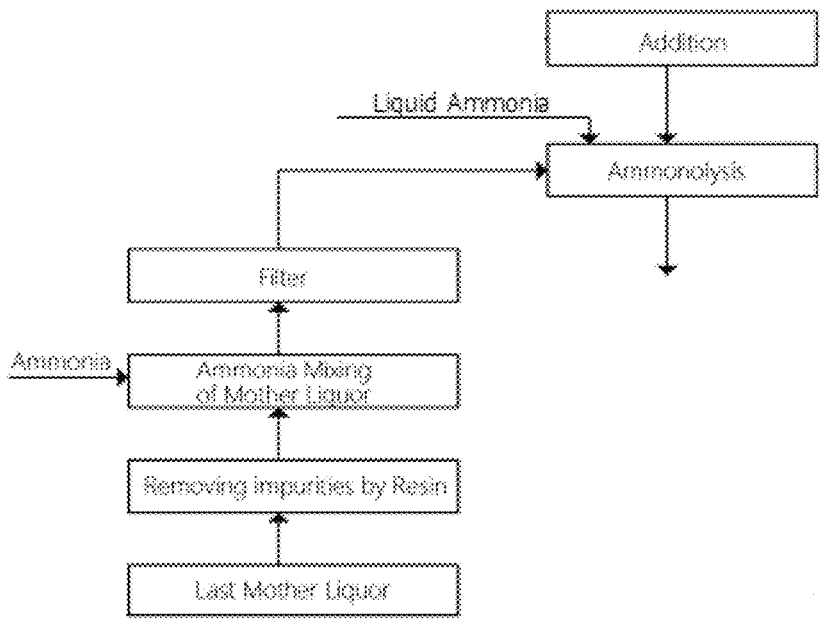
FIG. 1 is a process flow chart for removing impurities and recycling the mother liquor in accordance with one embodiment of the present disclosure.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

As shown in FIG. 1, the present disclosure provides a method for removing impurities from the mother liquor of taurine, which can be applied to the ethylene oxide process for preparing taurine. The last mother liquor of taurine obtained by multiple concentrations and crystallizations is passed through an anion exchange resin to be ion exchanged. An alkaline solution is then used to elute and regenerate the anion exchange resin, and the outlet material liquor is collected. The collected outlet material liquor is subjected to ammonia mixing treatment, and solid-liquid filtration separation to generate the impurity-removed mother liquor. The mother liquor is then returned to the ammonolysis step as a raw material.

Figure 2:
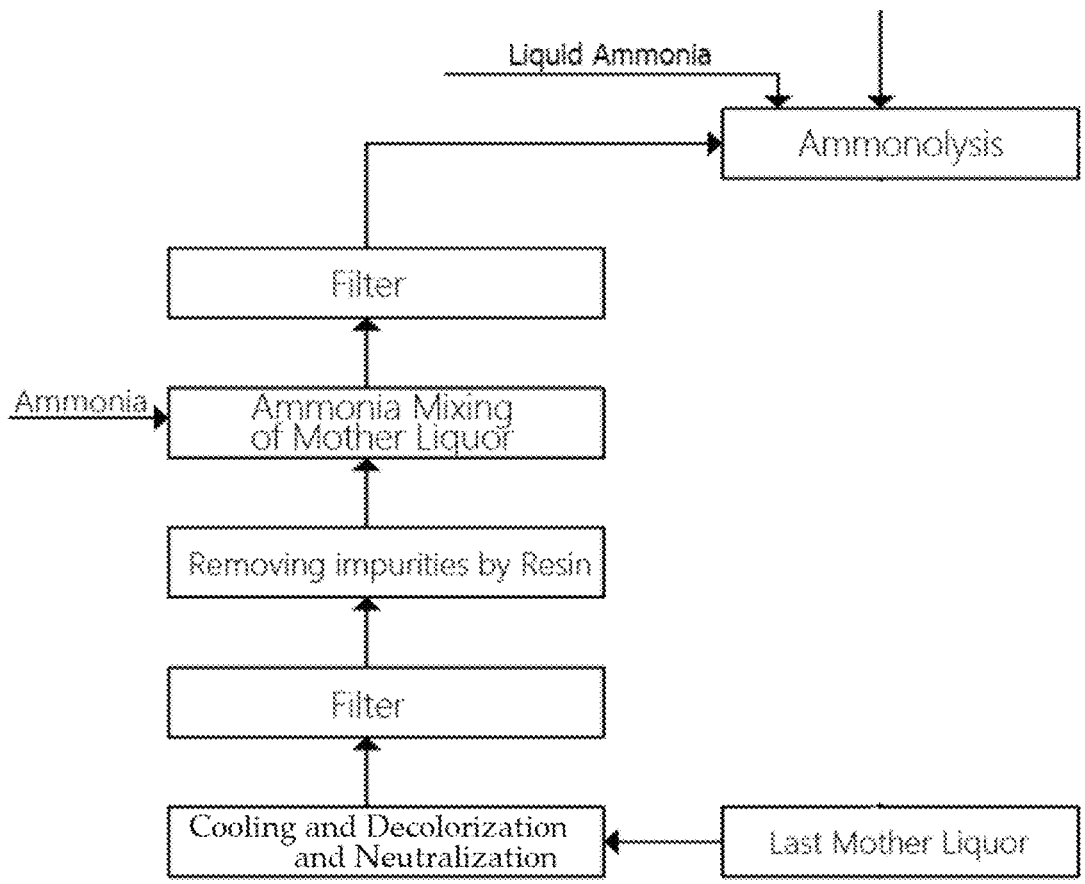
FIG. 2 is a process flow chart of a second embodiment of the present disclosure.

As shown in FIG. 2, in one particular method of the present disclosure for removing impurities and recovering taurine mother liquor, a step is added to the process of FIG. 1, namely an activated carbon decolorization and impurity removal step. This step can be the first step of removing impurities, that is, lowering down the temperature of the last mother liquor of taurine first, and then decolorization and removing impurities by activated carbon, solid-liquid filtration and separation, and then the process of anion resin adsorption is performed to further remove impurities. After filtration, an ammonia mixing treatment removes the sulfate in the mother liquor, and the impurity removal process for the mother liquor is completed, and it is returned to the ammonia hydrolysis process to join the production cycle.

Figure 3:
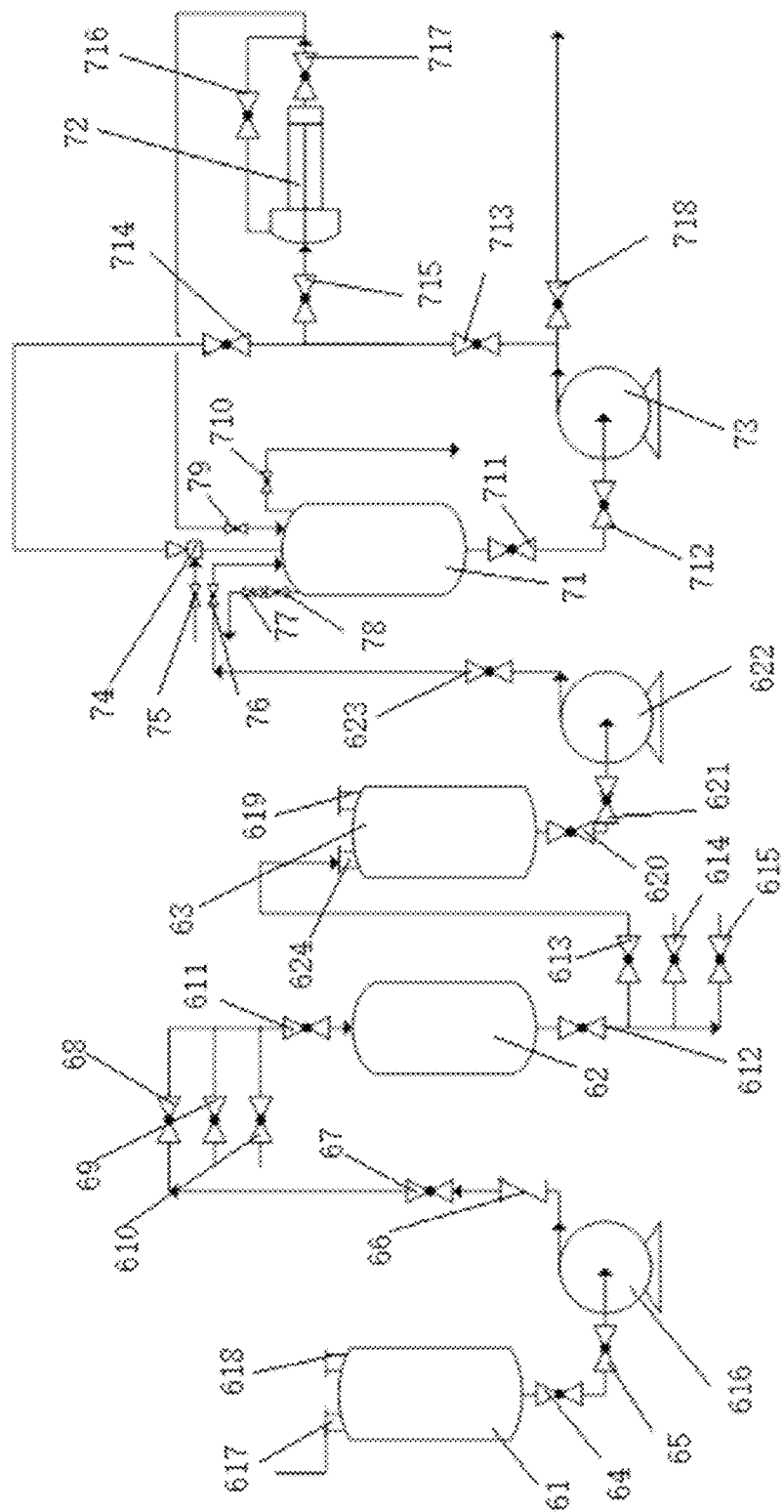
FIG. 3 is a schematic diagram of a mother liquor impurity removal and recovery system for use in performing the process of FIG. 1.

As shown in FIG. 3, the present disclosure provides a taurine mother liquor impurity removal and recovery system, utilizing the impurity removal and recovery method shown in FIG. 1. The system of FIG. 3 includes an anion resin adsorption device and an ammonia mixing and desalination device connected sequentially.

Among them, the feed port 617 of the anion resin adsorption device is connected to the outlet of the last mother liquor of taurine generated in the previous step of the taurine production process. The anion resin adsorption device includes a raw material tank 61, an anion exchange resin column 62, a receiving tank 63, and a raw material pump 616 connected between the raw material tank 61 and the anion exchange resin column 62. Both raw material tank 61 and receiving tank 63 are atmospheric pressure equipment.

The mother liquor feed port 617 and an exhaust port 618 are provided above the raw material tank 61, and a discharge valve 64 is provided below. Raw material pump 616 is provided with a feed valve 65, a discharge check valve 66 and a discharge valve 67. Above the column of the anion exchange resin, mother liquor feed valve 68, water washing valve 69 and regeneration feed valve 610 are arranged in parallel. The liquid from the three valves is controlled to enter the anion exchange resin column 62 by a total feed valve 611. The anion exchange resin column 62 is provided with a general discharge valve 612, which controls a regeneration discharge valve 613, a washing water discharge valve 614, and a material discharge valve 615 arranged in parallel. Inlet port 624 above receiving tank 63 connects with the pipeline of regeneration discharge valve 613, and discharge valve 620 is provided at the bottom, which is connected to inlet valve 621 of transit pump 622. Transit pump 622 is provided with transit outlet valve 623, and an exhaust port 619 is provided above receiving tank 63. Anion exchange resin column 62 controls the addition of the alkaline liquid through regeneration feed valve 610, and the anion adsorbed on the anion exchange resin column 62 is eluted in a regeneration manner and collected into mother liquor receiving tank 63. The material discharged from mother liquor receiving tank 63 is controlled and transferred to the feed port of the ammonia mixing and desalination device by transfer pump outlet valve 623 of the transfer pump. In addition to the pipeline valves, the system is also provided with some additional valves and connection components necessary for production equipment that are not shown. These can be common devices and apparatus and are not described in detail herein.

The anion resin adsorption device can remove most of the impurities in the last mother liquor, and the operation process is straightforward. During operation, the last mother liquor is added to raw material tank 61 through raw material tank feed port 617, and raw material tank discharge valve 64, raw material pump feed valve 65, raw material pump discharge valve 67, anion exchange resin column raw material feed valve 68, anion exchange resin column feed valve 611, anion exchange resin column discharge valve 612, and anion exchange resin column material discharge valve 615 are opened. The resin column raw material feed pump 616 is started and material will then be discharged from material discharge valve 615 of anion exchange resin column. The pH value at the outlet is observed, and the content of the outlet material detected. When the adsorption is saturated, the resin column raw material feed pump 616 is stopped, and the anion exchange resin column raw material feed valve 68 and anion exchange resin column material discharge valve 615 are closed. The anion exchange resin column washing water discharge valve 614 and anion exchange resin column water washing valve 69 are opened, and after cleaning for the pre-set time, the anion exchange resin column washing water discharge valve 614 and anion exchange resin column water washing valve 69 are closed. Next, the anion resin column regeneration discharge valve 613 and anion exchange resin column regeneration feed valve 610 are opened, and the resin is regenerated with alkali. The effective components in the mother liquor adsorbed on the resin are eluted at the same time, and the eluted mother liquor is sent to receiving tank 63. The exhaust port of the atmospheric pressure device is in the status of normal open.

The ammonia mixing and desalination device includes ammonia mixing reaction tank 71, a pump 73, and a leaf filter 72 connected sequentially. The leaf filter 72 can also be replaced by a sealed plate and frame filter. Ammonia absorber 74, ammonia inlet valve 75, feed valve 76, clear liquor return tank valve 79, emptying valve 710, safety valve 77 and front safety valve control valve 78 are located above the ammonia mixing tank 71. At the bottom of the ammonia mixing reaction tank is a discharge valve 711, which is connected to pump feed valve 712. At the other end of the pump 73 is a pump discharge valve 713 and transit discharge valve 718. The outlet of pump discharge valve 713 is connected to ammonia absorber 74 through return valve 714 and is connected to leaf filter 72 through inlet valve 715. The leaf filter is provided with overflow valve 716 and discharge valve 717; and discharge valve 717 is connected to clear liquor return tank valve 79. As before, some additional valves and connection components necessary for production equipment and common in the art are also provided in the device, but are not shown.

The ammonia mixing and desalination device can remove salts and impurities in the mother liquor, and the operation process is straightforward. Operation method: open front control valve 78 of safety valve, open emptying valve 710, open feed valve 76 to add mother liquor to ammonia mixing reaction tank 71, and close feed valve 76 after feeding. Open discharge valve 711 at the bottom, pump feed valve 712, and return valve 714; start pump 73, open pump discharge valve 713, open ammonia inlet valve 75 after stabilization, close emptying valve 710, and absorb ammonia until the content of ammonia is more than 15% (mass-volume ratio, 15 g/100 ml), then stop absorption and close ammonia inlet valve 75; open overflow valve 716 of leaf filter 72, clear liquor return tank valve 79, and inlet valve 715. After leaf filter 72 is filled, open the leaf filter discharge valve 717, and close overflow valve 716 of leaf filter at the same time. During this cycle, samples can be taken for observing the state of the materials in the ammonia mixing reaction tank 71 until the filtrate is clear. After filtrate is clear, open transit discharge valve 718 to transfer (recycle) the material to the ammonolysis reaction process.

Figure 4:
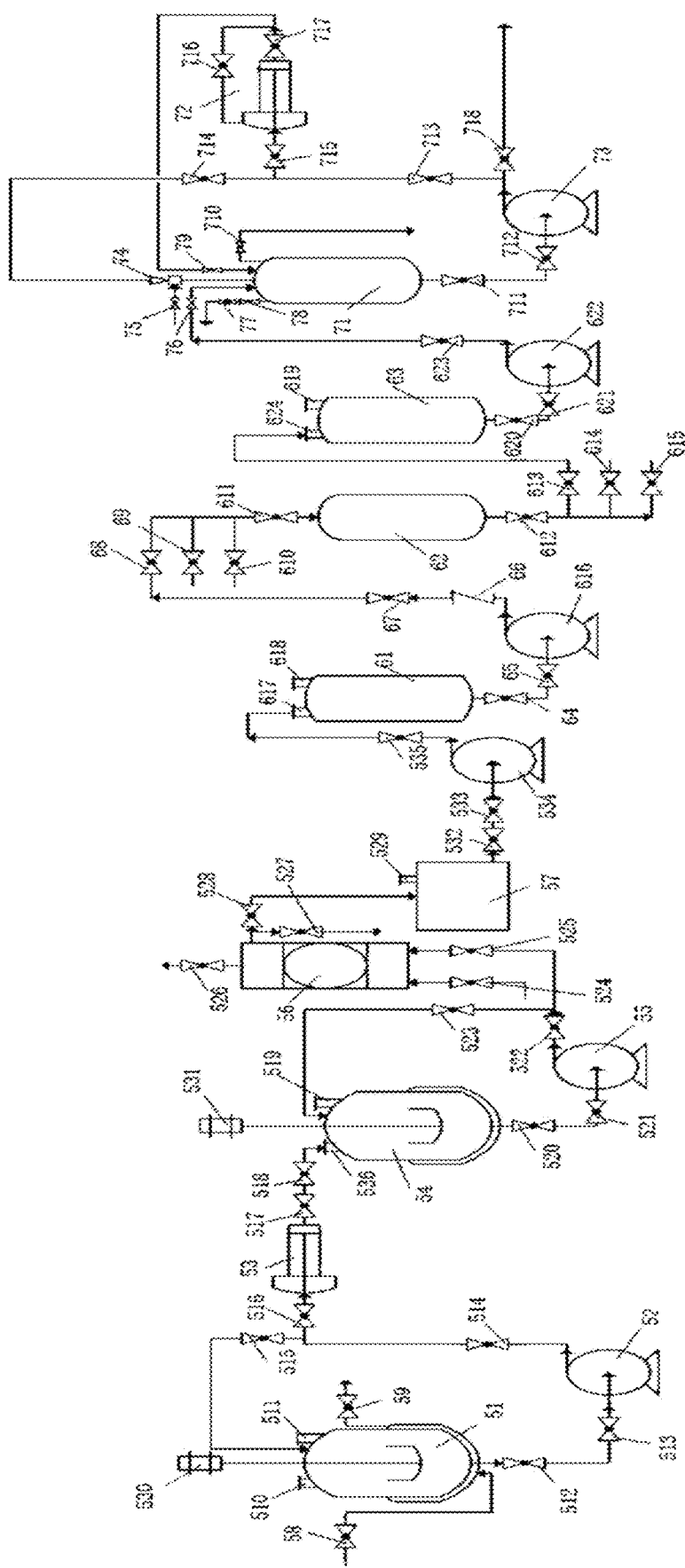
FIG. 4 is a schematic diagram of a mother liquor impurity removal and recovery system for use in preforming the process of FIG. 2, wherein an activated carbon decolorization and impurity removal device has been added to the system of FIG. 3.

For the taurine mother liquor impurity removal and recovery method shown in FIG. 2, an exemplary process system is shown in FIG. 4. Compared with the impurity removal and recovery system of FIG. 3, an activated carbon decolorization and impurity removal device is added upstream of the anion resin adsorption device. That is, the last mother liquor of taurine from the taurine production process is first decolorized and impurities removed by activated carbon. The thus treated last mother liquor is then sent to the anion resin adsorption device for adsorption treatment. Specifically, the activated carbon decolorization and removing impurity device includes a decolorization tank 51, a plate and frame filter pump 52, a plate and frame filter 53, a transit tank 54, a precision filter pump 55, a precision filter 56, a receiving tank 57, and a transfer pump 534, which are connected sequentially. Compared with the plate and frame filter 53, the pore diameter of the precision (or fine) filter 56 is smaller and can filter out small particles of impurities. Among them, decolorization tank 51, transit tank 54 and receiving storage tank 57 are all atmospheric pressure equipment.

A water circulation condensation layer is provided on the outside of decolorization tank 51 to reduce the temperature in the decolorization tank 51. The water circulation condensation layer (or water jacket) is provided with a cooling water inlet valve 58 and a cooling water outlet valve 59. The decolorization tank 51 is provided with a stirring mechanism 530. Mother liquor feed port 510 and exhaust port 511 are provided at the top of the decolorization tank 51 while the discharge valve 512 is provided at the bottom. The discharge valve 512 is connected to the plate and frame filter pump 52 through the plate and frame filter pump feed valve 513, and the plate and frame filter pump 52 is provided with a discharge valve 514 and return valve 515. The inlet and outlet of plate and frame filter 53 are provided with a feed valve 516 and a discharge valve 517 respectively, and is connected to transit tank 54 through transit tank feed valve 518. Above transit tank 54, a set discharge port 536, exhaust port 519 and stirring mechanism 531 are also provided. Discharge valve 520 at the bottom of the transit tank 54 is connected to precision filter pump feed valve 521, and the outlet of the precision filter pump 55 is connected to a discharge valve 522, which is connected to precision filter pump return valve 523 and a precision filter feed valve 525 respectively. A set inlet cleaning water valve 524, outlet cleaning water valve 527 and exhaust valve 526 are provided for the precision filter 56, and discharge valve 528 of the precision filter outlet is connected to the inlet of receiving tank 57. Receiving tank 57 is provided with an exhaust port 529, and its discharge valve 532 is connected to the inlet valve 533 of transit pump 534. Outlet valve 535 of transit pump 534 is connected to raw material tank 61 of the anion resin adsorption device. Valves and connecting components necessary for other production equipment are common in the art and will not be repeated here. A feed port for adding liquid acid is preferably provided on the decolorization tank to add liquid acid such as sulfuric acid, in order to reduce the pH of the solution in the tank, which is more conducive to subsequent impurity removal.

The addition of the activated carbon decolorization and impurity removal device in FIG. 4 improves the filtration efficiency and processing capacity through two-stage filtration. Operation method: Activated carbon is added from mother liquor feed port 510, or can be added from other openings, which is not limited here; the plate and frame filter decolorization tank discharge valve 512 is closed, and the last mother liquor of taurine (obtained in step S4) is added to the decolorization tank 51 through decolorization tank feed port 510; open cooling water outlet valve 59 and cooling water inlet valve 58 and pass in the cooling water to lower down temperature, and, at the same time, operate decolorization tank stirring mechanism 530 to cool down to the prescribed temperature; then close cooling water inlet valve 58 and cooling water outlet valve 59. Open decolorization tank discharge valve 512, plate and frame filter pump feed valve 513, plate and frame feed valve 516, plate and frame discharge valve 517, and transit tank feed valve 518; close transit tank discharge valve 520, and start plate and frame filter pump 52, and then adjust the plate and frame pressure through the plate and frame filter pump return valve 515. Activated carbon and last mother liquor of taurine enter plate and frame filter 53 together, then, activated carbon is trapped in filter 53. The plate and frame filter can be opened later so that the activated carbon that has absorbed impurities can be discharged. After the material in the transit tank 54 reaches a certain volume, open transit tank discharge valve 520, precision filter pump feed valve 521, precision filter pump return valve 523, precision filter feed valve 525, precision filter exhaust valve 526 and precision filter discharge valve 528; start precision filter pump 55, open precision filter pump discharge valve 522, and, after the precision filter exhaust valve 526 discharges, close precision filter exhaust valve 526; the feeding pressure of precision filter 56 is adjusted by precision filter pump return valve 523. The material collected by receiving tank 57 is sent to the subsequent processing station, that is, it is sent to raw material tank 61 of the anion resin adsorption device. After it is processed by the anion exchange resin column 62, send it to ammonia mixing reaction tank 71 for ammonia mixing treatment to remove sulfates and other impurities further, as described in connection with FIG. 3.

Figure 5:
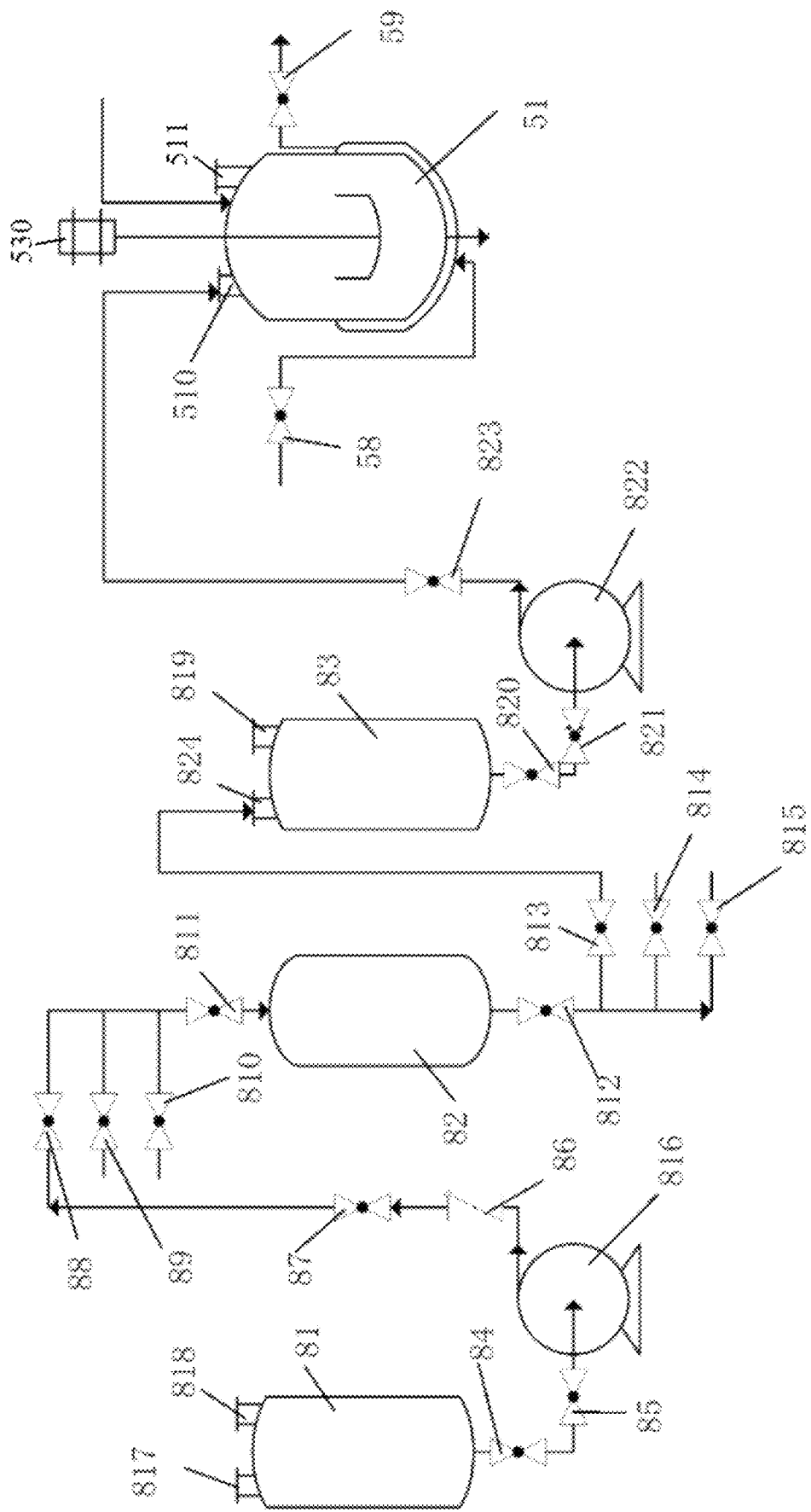
FIG. 5 is a schematic diagram of a portion of another embodiment of a mother liquor impurity removal and recovery system of the present disclosure, wherein an acidic cation exchange resin adsorption device has been added upstream of the activated carbon decolorization and impurity removal device (with the decolorization tank 51 included for clarity)

As shown in FIG. 5, embodiments of the present disclosure further optimize the impurity removal and recovery system. Instead of adding liquid acid to the decolorization tank to lower the pH, the last mother liquor of taurine obtained from the previous process is first treated with solid acid to reduce the pH. In one embodiment, the treatment device used for this purpose is an acidic cation exchange resin adsorption device, with the acid cation exchange resin adsorption device connected to the discharge port of the last mother liquor of taurine from the taurine production process.

As shown in FIG. 5, the cationic resin adsorption device includes a raw material tank 81, a cation exchange resin column 82, and a receiving tank 83. A raw material pump 816 is connected between the raw material tank 81 and the cation exchange resin column 82. The raw material tank 81 and the receiving tank 83 are atmospheric pressure equipment.

Above raw material tank 81, sits mother liquor feeding port 817 and an exhaust port 818; under raw material tank 81, sits discharging valve 84. The raw material pump 816 is provided with feed valve 85, discharge check valve 86 and discharge valve 87. Above cation exchange resin column 82, there is a mother liquor feed valve 88, a water washing valve 89 and a regeneration feed valve 810. The liquid in the three valves is controlled by total feed valve 811 and enters the cation exchange resin column 82. Cation exchange resin column 82 is provided with a general discharge valve 812, as well as a material discharge valve 813, a washing water discharge valve 814, and a regeneration discharge valve 815, all of which are controlled by general discharge valve 812, and arranged in parallel. Inlet 824 above the receiving tank 83 connects with the pipeline of material discharge valve 813. A discharge valve 820 is set below the receiving tank 83 and is connected to inlet valve 821 of transit pump 822. The transit pump is provided with a transit outlet valve 823. Exhaust port 819 is provided above the receiving tank 83. Cation exchange resin column 82 controls the addition of an acidic liquid through the regeneration feed valve 810, and the metal ions and the like adsorbed on the cation exchange resin column 82 are eluted and removed in a regeneration manner using the acidic liquid. The treated material is controlled to be transferred to feed port 510 of the decolorization tank 51 through transit valve 823 of transit pump 822. In addition to the pipeline valves described above, the system of FIG. 5 is also provided with additional conventional valves and connection components necessary for production equipment, which are not shown in FIG. 5.

The cationic resin adsorption device can remove impurities such as metal ions in the mother liquor and can reduce the pH of the mother liquor without introducing other anions or impurities, and the operation process is simple. Add the last mother liquor of taurine produced in the taurine production process to raw material tank 81 through raw material tank feed port 817. Open raw material tank discharge valve 84, raw material pump feed valve 85, raw material pump discharge valve 87, feed valve 88 of the cationic resin column 82, total feed valve 811 of the cationic resin column 82, cationic resin column discharge valve 812, and cationic resin column material discharge valve 813. Start the resin column raw material feed pump 816, and wait for the material to be discharged from the cationic resin column material discharge valve 813 to receiving tank 83, while observing the pH value at the outlet and detecting the content of the material at the outlet. When the pH at the outlet or the pH at receiving tank 83 meets the requirement, stop the resin column raw material feed pump 816, and close cationic resin column raw material feed valve 88 and cationic resin column material discharge valve 813. Open cationic resin column water discharge valve 814 and cationic resin column water wash valve 89, and after cleaning for a prescribed time, close cationic resin column wash water discharge valve 814 and cationic resin column water wash valve 89. Open cationic resin column regeneration discharge valve 815 and the cationic resin column regeneration feed valve 810, and regenerate the cationic resin column with acid. Metal ions and the other impurities adsorbed from the mother liquor onto the cation exchange resin are eluted from the column 82. The mother liquor processed in receiving tank 83 is transferred to decolorization tank 51 by transit pump 822.

Figure 6:
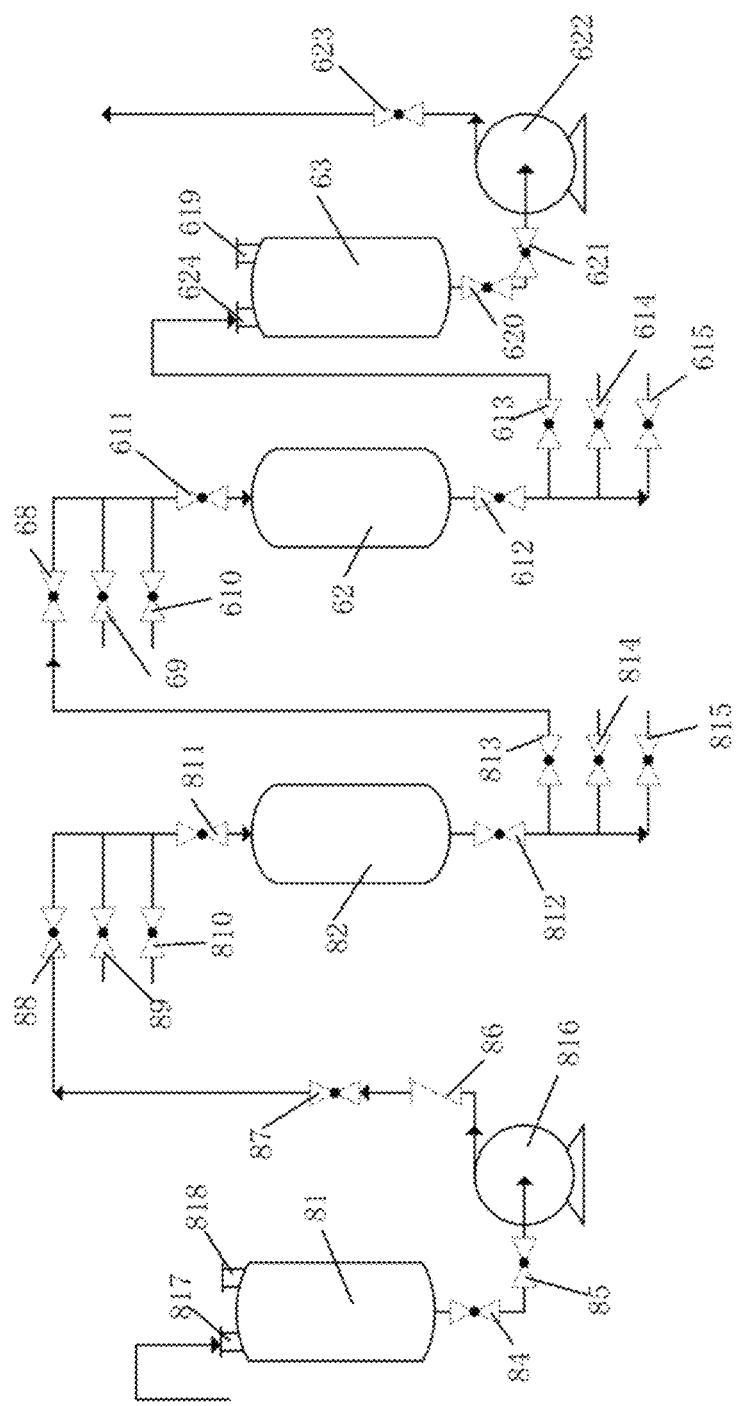
FIG. 6 is a schematic diagram of yet another embodiment of a mother liquor impurity removal and recovery system of the present disclosure.

FIG. 6 depicts an alternative embodiment of the present disclosure. The impurity removal and recovery system of FIG. 6 is composed of the activated carbon decolorization and impurity removal device of FIG. 4 (not shown in FIG. 6), a cation exchange resin adsorption device, an anion exchange resin adsorption device, and the ammonia mixing desalination device of FIG. 4 (not shown in FIG. 6). Among them, the cation exchange resin adsorption device and the anion exchange resin adsorption device share a raw material tank and receiving tank. The pH value of the last mother liquor of taurine after treatment is reduced by solid acid. This process involves two chemical reactions, one is the reaction between an acidic resin and cation in solution, and the other is the reaction between acid and a basic resin. After the stepwise reaction, the required materials are collected, and the separation is carried out to achieve complete separation.

Specifically, raw material tank 81 of the cation exchange resin adsorption device is connected to the receiving tank 57 of the activated carbon decolorization and impurity removal device (see FIG. 4). Raw material pump 816 is connected between raw material tank 81 and cation exchange resin column 82, cation exchange resin column 82 and anion exchange resin column 62 are connected, and anion exchange resin column 62 is connected to receiving tank 63. Receiving tank 63 is controlled to be fed to the feed port of the ammonia mixing and desalination device through transit outlet valve 623 of transfer pump 622 (i.e., for transferring discharged material discharged to the feed port of the ammonia mixing and desalination device of FIG. 4). In essence, the system shown in FIG. 6 will replace the components located between outlet valve 535 of the activated carbon decolorization and impurity removal device and the feed valve 76 of the ammonia mixing and desalination device in the system of FIG. 4. As compared to the system of FIG. 5, in FIG. 6 the cation exchange resin adsorption device is located downstream of the activated carbon decolorization and impurity removal device.

A mother liquor feed port 817 and an exhaust port 818 are provided above the raw material tank 81, and a discharge valve 84 is provided below; a raw material pump 816 is provided with a feed valve 85, a discharge check valve 86, and a discharge valve 87. Above cation exchange resin column 82 sit a mother liquor feed valve 88, a water washing valve 89 and a regeneration feed valve 810. The liquid in these three valves is controlled by a general feed valve 811 to enter the cation exchange resin column 82. The cation exchange resin column 82 is provided with a general discharge valve 812, a control material discharge valve 813, a washing water discharge valve 814, and a regeneration discharge valve 815; the material discharge valve 813, washing water discharge valve 814, and regeneration discharge valve 815 are arranged in parallel. The feed port above the anion exchange resin column connects with the pipeline of material discharge valve 813 and is controlled by mother liquor feed valve 68; water washing valve 69 and regeneration feed valve 610 are also set above the anion exchange resin column, with the liquid in the three valves controlled by general feed valve 611 to enter the anion exchange resin column 62. The anion exchange resin column 62 is provided with general discharge valve 612, which controls regeneration discharge valve 613, washing water discharge valve 614, and material discharge valve 615; the regeneration discharge valve 613, washing water discharge valve 614, and material discharge valve 615 are arranged in parallel. Inlet 624 above the receiving tank 63 connects with the pipeline of regeneration discharge valve 613; discharge valve 620 is provided below receiving tank 63 and is connected to inlet valve 621 of transit pump 622, and transit pump is provided with transfer outlet valve 623. Anion exchange resin column 62 controls the addition of alkaline liquid through regeneration feed valve 610, and the anion adsorbed on the anion exchange resin column 62 is eluted in a regeneration manner, and then collected in the mother liquor receiving tank 63; the discharge material of the mother liquor receiving tank 63 is controlled to be transferred to the feed port of the ammonia mixing and desalination device through the transit pump outlet valve 623 of the transfer pump.

Figure 7:
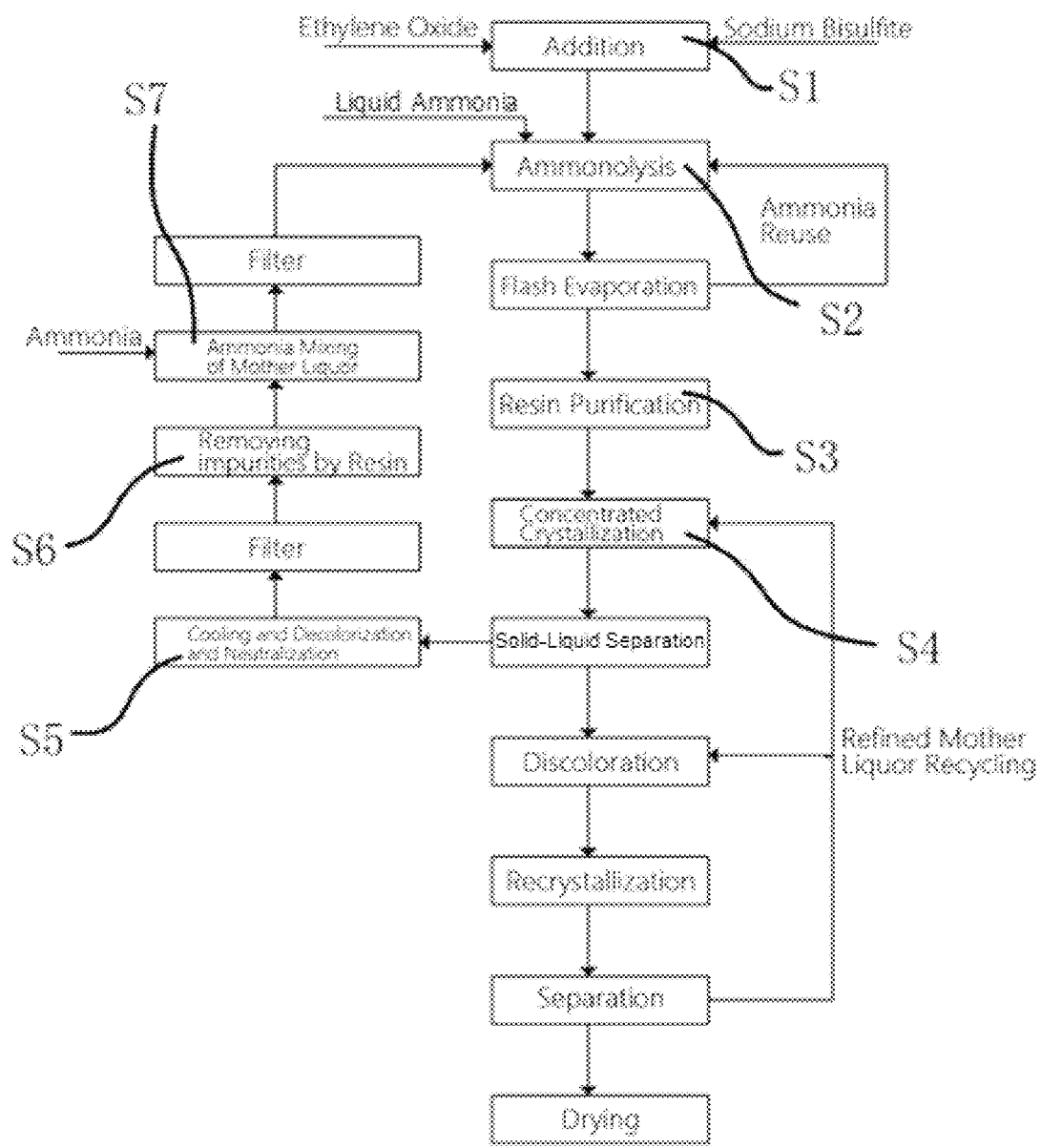
FIG. 7 is a process flow chart of the ethylene oxide process of taurine production process (cation exchange process) of the present disclosure.
Figure 8:
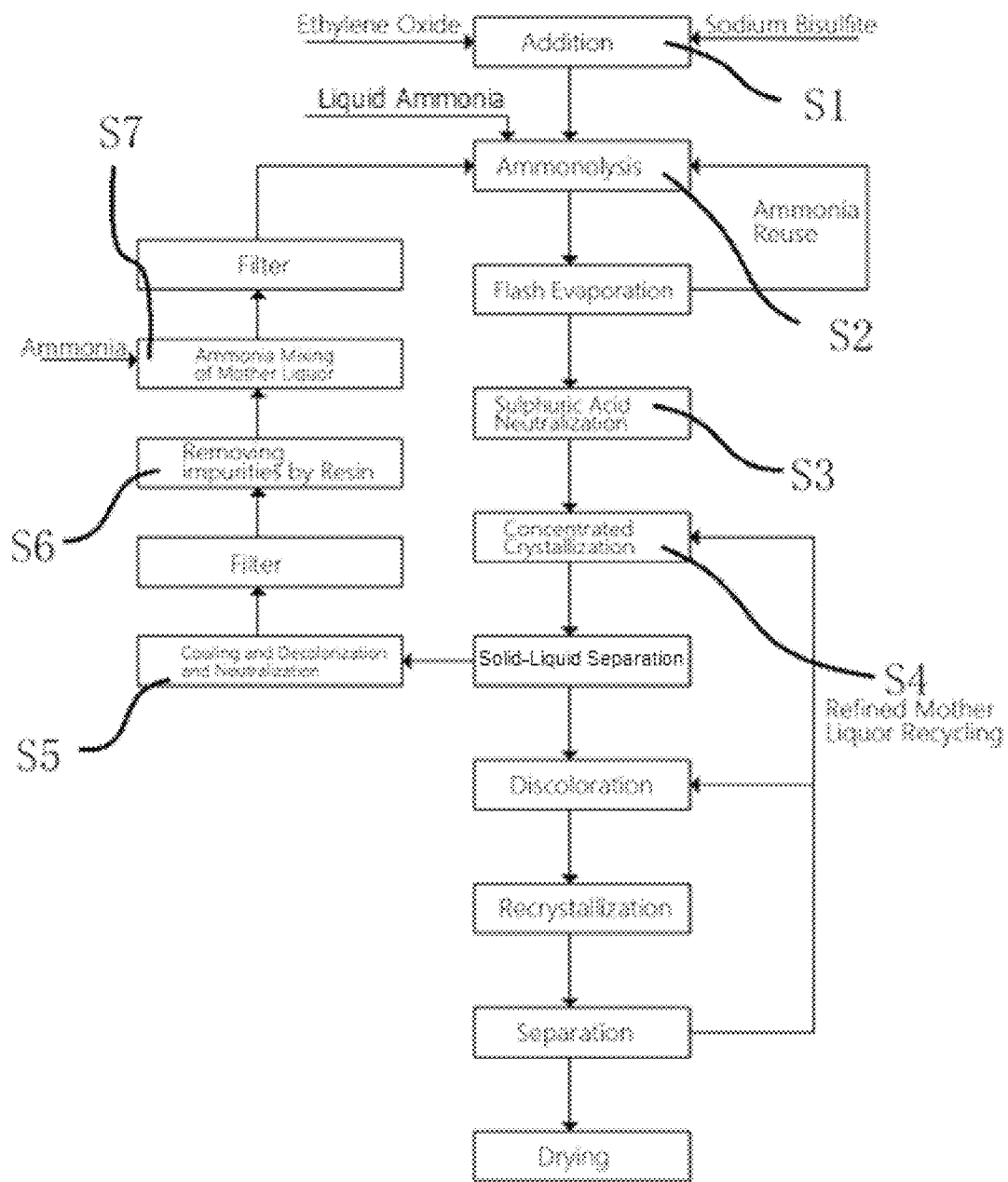
FIG. 8 is a process flow chart of the ethylene oxide process of taurine production process (sulfuric acid neutralization process) of the present disclosure.

As shown in FIG. 7 and FIG. 8, the present disclosure provides two processes for producing taurine by the ethylene oxide process, and the methods and systems for removing impurities are applied. The difference between the two methods lies in different post-ammonolysis processes: one uses a cationic resin process, as described in detail in Applicant's Chinese invention patent CN107056659, while the other method uses a sulfuric acid neutralization process. In the following embodiments, each step in the taurine mother liquor impurity removal and recovery method provided by the present disclosure is decomposed, and each embodiment is a step or part of a step in the method. The two processes shown in FIG. 7 and FIG. 8 are combined below to illustrate the taurine production process.

S1. Ethylene oxide is reacted with sodium bisulfate solution to generate sodium isethionate; in this step, impurities such as ethylene glycol and polyethylene glycol are generated.

S2. sodium isethionate obtained from S1, recycled mother liquor after the impurity removal treatment and ammonia (e.g., ammonia water) are mixed to generate the reaction solution, and then ammonia is absorbed to a certain concentration, and ammonolysis is carried out under the action of catalyst. After the reaction is completed, flash evaporation is performed to remove excess ammonia gas from the reaction solution and the discharged ammonia is recycled and used as a raw material for the ammonolysis reaction. The solution is then concentrated by evaporation to generate a sodium taurate solution. The ethylene glycol by-products in the sodium isethionate solution in step S1 are converted into organic impurities such as polyether alcohols. Because the ammonolysis reaction is reversible, according to the theory of chemical equilibrium, the presence of sodium ditaurate and sodium tritaurate can achieve the purpose of improving the conversion of raw materials. Recycling the mother liquor after the impurity removal treatment can achieve the purpose of increasing the application of liquor and reducing the side reaction, thereby achieving the purpose of further stabilizing production and improving yield.

S3. The sodium taurate solution generated in S2 is prepared to a certain concentration, and a slurry of taurine is generated by either: (a) passing the solution through the acidic cation exchange resin column; or (b) using a sulfuric acid neutralization process by adding sulfuric acid until the pH is 7.0-8.5.

S4. When S3 uses an acidic cation exchange resin, the slurry of taurine is concentrated and crystallized, followed by separation of crude taurine from the mother liquor at a separation temperature of about 15-25° C.; when S3 uses a sulfuric acid neutralization process, the slurry of taurine is cooled and crystallized, followed by separation of crude taurine from the mother liquor at a separation temperature of about 32-35° C. Thereafter, in either instance the mother liquor is further concentrated (water evaporated), cooled, and crystallized for multiple times, and additional taurine separated and extracted each time through equipment such as plate and frame filter. Finally, the last mother liquor of taurine is concentrated.

S5. First, the last mother liquor of taurine collected in S4 is cooled to 15-25° C. to generate the best crystallization effect and precipitate impurities. Then, a certain amount of activated carbon is added, the solid impurities filtered out through equipment such as a plate and frame device with a microporous filter to generate the mother liquor after impurity removal. In this step, the pH value of the solution needs to be adjusted to be acidic or neutral, and two methods can be used. One method is to add liquid acid, such as sulfuric acid, to adjust the pH value of the solution to 2.5-7.0. Another method is to treat the last mother liquor of taurine with an acidic cation exchange resin to adjust the pH value to 3.0-6.0, as further described below.

S6. Pass the mother liquor collected in S5 through the alkali anion exchange resin column. The liquid material at the collection outlet contains a lot of impurities and needs subsequent treatment. After the impurity-containing discharged liquid is collected to a certain extent, an alkaline solution, such as liquid alkali, is then used to regenerate the resin column. In this instance, the liquid material at the collection outlet is the mother liquor containing taurine that has been thoroughly decontaminated. The pH value of the solution is controlled so that most of the taurine in the mother liquor fed to the anion exchange resin column exists in anion form, according to the principle of anion resin adsorption. The resin exchanges with the taurine anion and adsorbs the taurine anion onto the resin. At the same time, sodium isethionate, sodium ditaurate, and sodium tritaurate in the mother liquor also exist in anion form, and therefore can also exchange with the resin, and are adsorbed on the resin. Organic impurities such as ethylene glycol and polyether alcohol, however, do not exchange with the resin and cannot be adsorbed by the resin. Following discharge of the impurity-containing liquid, taurine and sodium isethionate adsorbed on the resin are eluted through an alkaline solution to generate pure taurine mother liquor, so as to achieve the separation of effective ingredients and impurities, to fulfill the purpose of removing impurities from the mother liquor.

S7. Pass the thoroughly decontaminated taurine-containing mother liquor collected in S6 into liquid ammonia under cooling conditions, and until the ammonia content is greater than 15%. A large amount of sulfate and other impurities will be precipitated, and the clear mother liquor can then be filtered by means of leaf filter or a sealed plate and frame filter. The mother liquor generated then can be recycled to the ammonolysis step (Step S2). The filtering device needs to meet environmental protection requirements and must be sealed to prevent ammonia leakage.

The process principle of the cation exchange resin in Step S5 is explained below:

The acidic cation exchange resin in step S5 can be regarded as solid acid. The chemical reactions that occur with cation exchange resins are as follows (cations are only represented by $Na^+$, and regeneration acids are only represented by $H_2SO_4$):

$$RH+Na^+ \rightarrow R_{na}+H^+ \quad (1)$$

$$2Rna+H_2SO_4 \rightarrow 2RH+Na_2SO_4 \quad (2)$$

Among them, RH indicates that the acidic cation exchange resin is in a hydrogen state (that is, a state where regeneration is completed), and Rna indicates that the acidic cation exchange resin is in a sodium-absorbing state (that is, a state after being saturated). The principle of regenerated cation exchange resin is that the cations in the solution have affinity with the groups opposite to the electricity on the resin, so the cations in the solution remain on the resin, and the hydrogen ions dissociated in the resin are released to the solution and combine with the anions in the solution. The reaction solution can be fully exchanged with the cationic resin to achieve the purpose of lowering the pH value of the solution. When the adsorption is to a certain extent, the pH value of the solution reaches the lowest. After the cation exchange resin is saturated, it needs to be more acidic (that is, the acidity of $H_2SO_4$ in chemical Formula (2) is stronger than that of RH). The regeneration solution exchanges the cations remaining on the resin again to generate RH. At the same time, the regeneration $Na_2SO_4$ will be separated out as a solution. In this way, RH can generate $H^+$ again, that is, it can continue to be used according to chemical Formula (1) above.

In order to illustrate the technical effects of the present disclosure, the following examples are used for explanation. Unless otherwise specified, the raw materials used in the following examples are all commercially available goods; unless otherwise specified, the methods used are conventional methods; unless otherwise specified, the material contents refer to mass percentage by volume.

Example 1

The content shown in this example is a method for processing an anion exchange resin column in step S6:

At the beginning of pretreatment, the anion exchange resin is loaded into the exchange column by the wet method, 2BV, 4% sodium hydroxide solution (mass percentage, the same below). passes the resin in the exchange column at a flow rate of 1.8-2.2 BV/h in the forward direction, and then deionized water is used to wash the acidity to pH value=9 or so. When packing the column, add the resin firstly to the measuring cylinder by wet method, the upper layer of the resin guarantees a water layer of about 5-10 cm, shock the graduated cylinder slightly to make the resin dense, and then transfer it into the exchange column by wet method, a 5-10 cm water layer should be left on the upper part of the resin layer, and no air bubbles should be left in the resin layer.

During the regeneration process, there is no column loading step, but water is directly added to drain the material from the resin column, and then 2 BV of 4% sodium hydroxide aqueous solution is passed through the resin in the exchange column in the forward direction at a flow rate of 2 BV/h. After charging 1 BV, the regeneration eluate is collected. Then, deionized water is used to wash the acidity to a pH of about 9 and the regeneration is completed. The washing water can be collected and mixed with the regenerated eluate, and the regenerated eluate mixed with the washing water can be used as the mother liquor containing taurine for subsequent reprocessing and reuse in the ammonolysis reaction.

Example 2

The content shown in this example is the taurine mother liquor generated after the impurity removal treatment of the last mother liquor of taurine according to the Step S5 and Step S6:

(1) Taurine mother liquor treatment: Take 1000 ml of taurine mother liquor (from S4), wherein the mass volume percentage of taurine is 10% (based on taurine, 100 ml of solution contains 10 g of taurine), lower temperature to 15-25° C., add 1 g of activated carbon, add sulfuric acid, adjust the pH to 3-3.5, and suction-filter to generate 950 ml of mother liquor.

(2) Take 500 ml of the above mother liquor from step (1) and pass it forward through the anion exchange resin column at a flow rate of 0.25-2.5 BV/h. Initially, water will come out of the outlet of the resin layer, and it may not need to be collected. It can be determined when material from the mother liquor not absorbed on the resin is coming out by monitoring the pH; the material from the mother liquor is flowing out when the pH changes. After the material from the mother liquor begins to flow out, start metering and collection, and sample every 0.08-0.15BV to monitor the pH value. When the pH of the collected material is basically the same as the mother liquor inlet (that is, the pH is close), stop feeding; then, use the deionized water to wash out the non-absorbed material from the mother liquor for recovery in a forward direction at a flow rate of 2BV/h again; after the non-absorbed materials are driven out, 2BV, 4% sodium hydroxide solution is then passed in a forward direction through the resin layer at a flow rate of 2BV/h, and the total volume of the collected material is about 820 ml. The main components of the eluate are taurine and sodium isethionate; the taurine content is 6% and the sodium isethionate content is 7.3%.

The testing data is as follows:

| Item | The last mother liquor of taurine (before treatment) | The last mother liquor of taurine (after treatment) |
|---|---|---|
| Ethylene glycol | 6% | 0.5% |
| Fe | 10 ppm | <1 ppm |
| Content of Taurine | 10% | 6% |
| Content of Sodium isethionate | 12% | 7.3% |
| Outer Appearance | Yellow | Light Yellow |

Example 3

The mother liquor of taurine, treated in accordance with Example 2 is subjected to ammonia mixing treatment (Step S7), and recycled.

Ammonia mixing treatment for recovery of mother liquor: The mother liquor collected in Example 2 is combined with liquid ammonia until its ammonia content reaches 15%-20%, and filtered to generate a transparent and clear solution. Based on testing, the treated mother liquor is essentially free of sulfate.

Preparation of sodium taurate: sodium hydroxide is used as catalyst, and the ammonolysis reaction is performed using a sodium isethionate solution, the mother liquor following treatment with ammonia, and ammonia gas, at 220-280° C. and 10-15 MPa; the ammonolysis reaction is performed for 1 hour. After the reaction is completed, the solution generated after the ammonia gas is removed by flash evaporation is a sodium taurate solution.

Example 4

A mother liquor of taurine containing 10% taurine (10 g taurine per 100 ml), without being treated in accordance with Example 2 is subjected to ammonia mixing treatment (Step S7), and recycled.

Ammonia mixing treatment for recovery of mother liquor: The raw material (that is, the mother liquor without treatment) is passed through ammonia until its ammonia content reaches 15%-20%, and filtered to generate a transparent and clear solution.

Preparation of sodium taurate: the sodium hydroxide is used as a catalyst, and the ammonolysis reaction is performed using a sodium isethionate solution, the mother liquor following treatment with ammonia, and ammonia gas. At 220-280° C. and 10-15 MPa, the ammonolysis reaction is performed for 1 hour. After the reaction is completed, the solution generated after the ammonia gas is removed by flash evaporation is a sodium taurate solution.

Example 5

Two sets of experiments according to the present disclosure and corresponding comparative experiments were selected to show the conditions of the ammonolysis reaction and the subsequent extraction of the crude taurine content under various mother liquor reuse conditions.

In the following examples, 1.5 moles of sodium isethionate was used, and a sodium taurate solution was prepared according to the methods of Example 3 or Example 4. The generated sodium taurate solution was treated with a cation exchange resin to generate a taurine solution, and then the taurine solution was concentrated, cooled, and crystallized to generate a crude taurine product, and the taurine content was measured.

The yield of the ammonolysis reaction was calculated according to the following formula:

Yield of ammonolysis reaction=the mass of pure taurine÷(Mass of sodium isethionate÷148×125)× 100%. The results are shown in the table below.

| SN of Experiment | Item | Mother Liquor Volume (ml) | Taurine content (g/ml) | Sodium isethionate content (g/ml) | Sodium isethionate Mass (g) | Sodium taurate solution The mass of pure taurine (g) | Yield of ammonolysis reaction Calculating by the sodium isethionate input | Crude taurine Mass (g) | Taurine Content (g/g) |
|---|---|---|---|---|---|---|---|---|---|
| 1 | Example 4 | 115 | 10% | 12% | 222 | 172.5 | 92.00% | 162.7 | 88% |
| 2 | Example 4 | 135 | 10% | 12% | 222 | 177.2 | 94.50% | 171 | 86% |
| 3 | Example 3 | 190 | 6% | 7.30% | 222 | 187.5 | 100.00% | 173.2 | 92% |
| 4 | Example 3 | 225 | 6% | 7.30% | 222 | 206.3 | 110.00% | 188.5 | 93% |

This comparative example shows that in the ammonolysis process, the taurine content in the crude taurine product can reach 92% or more when the last mother liquor of taurine treated in Step S5 and Step S6 is used for production.

By comparing Experiment 1 and Experiment 2, an increase in the application of the mother liquor not treated in accordance with S5 and S6 will increase the yield of the ammonolysis reaction; but at the same time, the crude taurine content will decrease, which will eventually affect the quality of the finished product, which means that the untreated mother liquor can only be used to a certain extent, and it is why the amount of mother liquor used in the alkylene oxide process route cannot continue to increase.

By comparing Experiment 1 and Experiment 3, and Experiment 2 and Experiment 4, the amount of the mother liquor with and without the S5/S6 treatment is the same (the same mass of taurine). However, by treating the mother liquor the yield of the ammonolysis reaction is significantly increased, and the taurine content in the crude product increases significantly. This fully demonstrates that impurities are removed from the mother liquor during the treatment, which causes the side reactions under the conditions of the ammonolysis reaction to be greatly reduced and the product quality to be greatly improved.

By comprehensively comparing Experiments 1, 2, 3, and 4 in this Example 5, the effect of the mother liquor after impurity removal treatment on improving the yield and the crude product content is very obvious; at the same time, the amount of mother liquor recycled after the treatment can obviously be increased.

Example 6

The content shown in this Example is the taurine mother liquor generated after the impurity removal treatment of the last mother liquor of taurine according to Step S5 and Step S6:

(1) Taurine mother liquor treatment: Take 1000 ml of taurine mother liquor, in which the mass volume percentage is 10% (based on taurine, 100 ml of the solution contains 10 g of taurine). Lower the temperature to 15-25° C., then add 1 g of activated carbon, adjust the solution pH to 3-3.5 by cation exchange resin treatment, and then concentrate and reduce the mother liquor to 950 ml.

(2) Take 500 ml of the above mother liquor from step (1) and pass it through the anion exchange resin column in a forward direction at a flow rate of 0.25-2.5BV/h. The initial water at the outlet comes from the resin layer, and is unnecessary to be collected. (It can be judged whether the material from the mother liquor flows out by detecting the pH Value, when the pH value changes, it indicates that the material from the mother liquor is flowing out.). After the material from the mother liquor comes begins to flow, start to measure and collect, and sample every 0.08-0.15BV to monitor the pH value. When the pH of the collected material is basically the same as the mother liquor intake (that is, the pH values are close), stop feeding; then use deionized water to clean and recover the non-absorbed material from the mother liquor in a forward direction at a flow rate of 2BV/h; wait until the material is exhausted. Then 2BV, 4% sodium hydroxide solution is passed through the resin layer in a forward direction at a flow rate of 2BV/h, and the total volume of the collected materials is about 820 ml. The main components of the eluate are taurine and sodium isethionate; the taurine content is 6.3% and the sodium isethionate content is 7.5%.

The testing data is as follows:

| Item | The last mother liquor of taurine (before treatment) | The last mother liquor of taurine (after treatment) |
|---|---|---|
| Ethylene glycol | 6% | 0.5% |
| Fe | 10 ppm | <0.5 ppm |
| Content of Taurine | 10% | 6.3% |
| Content of Sodium isethionate | 12% | 7.5% |
| Outer Appearance | Yellow | Colorless and light yellow |

Comparison of Example 2 and Example 6:
Before treatment: Taurine: 1000*10%=100 g;
Sodium isethionate: 1000*12%=120 g;
After treatment of Example 2:
taurine 950/500*820*6%=93.48 g
Sodium isethionate: 950/500*820*7.3%=113.73 g;
Taurine recovery rate=93.48/100*100%=93.48%
Sodium isethionate Recovery Rate=113.73/120*100%=94.78%
After treatment of Example 6:
taurine 950/500*820*6.3%=98.15 g
Sodium isethionate: 950/500*820*7.5%=116.85 g;
Taurine recovery rate=98.15/100*100%=98.15%
Sodium isethionate Recovery Rate=116.85/120*100%=97.38%

| | | Mother liquor | | | | Recovery Rate | |
| | | | Sodium | | | | |
| Item | Volume ml | Taurine content (g/ml) | isethionate content (g/ml) | Taurine Mass (g) | Sodium isethionate Mass (g) | Taurine (100%) | Sodium isethionate (100%) |
|---|---|---|---|---|---|---|---|
| Before Treatment | 1000 | 10% | 12% | 100.00 | 120.00 | | |
| After Treatment of Example 2 | 1558 | 6% | 7.30% | 93.48 | 113.73 | 93.48% | 94.78% |
| After Treatment of Example 6 | 1558 | 6% | 7.50% | 98.15 | 116.85 | 98.15% | 97.38% |

Note:
The volume of mother liquor after treatment = 950/500 * 820 = 1558 ml

It is found through experiments that the recovery rate is higher with cationic resin treatment than with sulfuric acid treatment, and the solution color is lighter.

It should be noted that the above embodiments and examples are only used to illustrate the technical solutions of this invention, not to limit it; although this invention has been described in detail with reference to the foregoing embodiments and examples, the ordinary technicians in this field should understand: the technical solutions described in the foregoing embodiments and examples could be modified, or the reaction conditions could be replaced, or some of the technical features could be replaced by equivalents; and the modifications or substitutions shall not deviate from the technical solutions, spirit and scope of the embodiments of this invention.

While various embodiments of the present disclosure have been described in detail above, it will be understood that the components, features and configurations, as well as the methods of manufacturing the devices and methods described herein are not limited to the specific embodiments described herein.

What is claimed is:

1. A method for removing impurities from the last mother liquor of taurine in an ethylene oxide production process for producing taurine, said production process including the ammonolysis of sodium isethionate, wherein the last mother liquor of taurine includes taurine, sodium isethionate, and impurities, comprising the following steps:
   (a) decolorizing, under cooling conditions, the last mother liquor of taurine by adding activated carbon to the last mother liquor, performing a solid-liquid separation to remove impurities from the last mother liquor, and adjusting the pH of the last mother liquor to acidic or neutral:
   (b) contacting the last mother liquor of taurine from step (a) with an anion exchange resin such that taurine anion and the anion of sodium isethionate are adsorbed on the anion exchange resin;
   (c) eluting and regenerating the anion exchange resin with an alkaline solution such that taurine anion and the anion of sodium isethionate are eluted from the anion exchange resin, and collecting the eluate;
   (d) subjecting the eluate to ammonia mixing treatment by adding ammonia thereto; and
   (e) separating the liquid in the treated eluate from impurities by solid-liquid separation in order to generate a treated mother liquor of taurine comprising taurine and sodium isethionate, and reduced impurities as compared to said last mother liquor of taurine.

2. The method according to claim 1, further comprising the step of returning the mother liquor generated in step (e) to the ammonolysis step of the production process.

3. The method according to claim 2, wherein during the said ammonia mixing treatment step, liquid ammonia or ammonia gas is added to the eluate until the ammonia concentration in the eluate is 15 g/100 ml or more.

4. The method according to claim 3, wherein the said anion exchange resin is an alkaline anion exchange resin.

5. The method according to claim 1, wherein the pH of the last mother liquor is adjusted by adding liquid acid or by treating the mother liquor with a cation exchange resin.

6. The method according to claim 1, wherein the temperature of the last mother liquor during decolorizing is controlled to be 15-25° C.

7. An ethylene oxide process for producing taurine, comprising the steps of:
   (a) reacting ethylene oxide with sodium bisulfite to generate sodium isethionate;
   (b) subjecting the sodium isethionate generated in step (a) and the treated mother liquor of taurine removed of impurities and recovered in step (f) to an ammonolysis reaction to generate a sodium taurate solution;
   (c) concentrating the sodium taurate solution of step (b) by evaporation to generate a concentrated sodium taurate solution;
   (d) generating crude taurine and a mother liquor by
      (i) acidifying the concentrated sodium taurate solution of step (c) using an acidic cation exchange resin to obtain a taurine solution, followed by concentration and crystallization of the taurine solution and thereafter separating the crude taurine from the mother liquor; or
      (ii) adding sulfuric acid to the concentrated sodium taurate solution of step (c) to obtain a taurine crystallization liquid, followed by cooling and crystallization of the taurine crystallization liquid and thereafter separating the crude taurine from the mother liquor;
   (e) concentrating and crystallizing the mother liquor from step (d) at least once, with taurine separated and extracted from the mother liquor after each crystallizing step, thereby generating a last mother liquor of taurine, wherein the last mother liquor includes taurine, sodium isethionate, and impurities; and
   (f) performing the method of claim 1 to remove impurities from the last mother liquor of taurine from step (e), and recycling the treated mother liquor to step (b).

8. The method of claim 1, wherein said alkaline solution comprises sodium hydroxide.

9. The method according to claim 5, wherein the pH of the last mother liquor is adjusted by treating the mother liquor with a cation exchange resin.

10. The method according to claim 5, wherein the pH of the last mother liquor is adjusted by adding liquid acid.

11. The method according to claim 7, wherein the step of generating crude taurine and a mother liquor comprises:
   acidifying the concentrated sodium taurate solution of step (c) using an acidic cation exchange resin to obtain a taurine solution, followed by concentration and crystallization of the taurine solution and thereafter separating the crude taurine from the mother liquor.

12. The method according to claim 7, wherein the step of generating crude taurine and a mother liquor comprises:
   adding sulfuric acid to the concentrated sodium taurate solution of step (c) to obtain a taurine crystallization liquid, followed by cooling and crystallization of the taurine crystallization liquid and thereafter separating the crude taurine from the mother liquor.

* * * * *